(12) United States Patent
Lopez

(10) Patent No.: US 11,744,299 B2
(45) Date of Patent: Sep. 5, 2023

(54) SAFETY-MONITORING GARMENT SYSTEM

(71) Applicant: Fabian Vincent Lopez, Pico Rivera, CA (US)

(72) Inventor: Fabian Vincent Lopez, Pico Rivera, CA (US)

(*) Notice: Subject to any disclaimer, the term of this patent is extended or adjusted under 35 U.S.C. 154(b) by 36 days.

(21) Appl. No.: 17/214,767

(22) Filed: Mar. 26, 2021

(65) Prior Publication Data

US 2021/0298371 A1 Sep. 30, 2021

Related U.S. Application Data

(60) Provisional application No. 63/000,377, filed on Mar. 26, 2020.

(51) Int. Cl.

| | |
|---|---|
| *A41D 13/01* | (2006.01) |
| *A41D 1/00* | (2018.01) |
| *A61B 5/01* | (2006.01) |
| *A61B 5/021* | (2006.01) |
| *A61B 5/024* | (2006.01) |

(Continued)

(52) U.S. Cl.
CPC .............. *A41D 13/01* (2013.01); *A41D 1/005* (2013.01); *A61B 5/01* (2013.01); *A61B 5/021* (2013.01); *A61B 5/024* (2013.01); *F21V 33/0008* (2013.01); *G02B 6/0008* (2013.01); *G06F 1/163* (2013.01); *A41D 1/002* (2013.01); *A61B 5/6804* (2013.01)

(58) Field of Classification Search
CPC ........ A41D 13/01; A41D 1/002; A41D 1/005; A61B 5/6804; A61B 5/01; A61B 5/021; A61B 5/024; F21V 33/0008; G02B 6/0008; G06F 1/163
See application file for complete search history.

(56) References Cited

U.S. PATENT DOCUMENTS

| | | | |
|---|---|---|---|
| 6,085,698 A | 7/2000 | Klein | |
| 6,605,038 B1 * | 8/2003 | Teller | ..................... A61B 5/411 |
| | | | 128/920 |

(Continued)

FOREIGN PATENT DOCUMENTS

| | | | | |
|---|---|---|---|---|
| CN | 108095212 A | * | 6/2018 | ............. A41D 1/005 |
| KR | 20180092126 A | * | 8/2018 | ............. A61B 5/024 |
| WO | WO2014186071 A1 | | 11/2014 | |

*Primary Examiner* — Alan B Cariaso

(57) ABSTRACT

A safety-monitoring garment system is used to thoroughly monitor the health and performance of a user. The system includes a garment, at least one health-monitoring sensor, at least one performance-tracking sensor, a microcontroller, a user controller, and a portable power source. The garment is preferably a jacket for the user. The at least one health-monitoring sensor continuously monitors the vitals of the user, and the at least one performance-tracking sensor monitors the performance status of the user. The microcontroller stores, analyzes, and delivers the data from the at least one health-monitoring sensor and the at least one performance-tracking sensor to an external computing device. The user controller manages the at least one health-monitoring sensor and the at least one performance-tracking sensor. The portable power source provides the necessary power for the at least one health-monitoring sensor, the at least one performance-tracking sensor, the microcontroller, and the user controller.

13 Claims, 4 Drawing Sheets

(51) Int. Cl.
    *F21V 33/00*     (2006.01)
    *F21V 8/00*     (2006.01)
    *G06F 1/16*     (2006.01)
    *A61B 5/00*     (2006.01)

(56) References Cited

U.S. PATENT DOCUMENTS

| | | |
|---|---|---|
| 6,834,395 B2 | 12/2004 | Fuentes |
| 6,997,573 B2 | 2/2006 | Maese |
| 9,888,729 B2 | 2/2018 | Kull et al. |
| 10,076,142 B2 | 9/2018 | Samuelsen et al. |
| 2008/0319279 A1* | 12/2008 | Ramsay ................ G16H 40/63 |
| | | 600/301 |
| 2014/0318699 A1* | 10/2014 | Longinotti-Buitoni ...................... |
| | | H05K 1/038 |
| | | 156/247 |
| 2015/0267911 A1* | 9/2015 | Cushnie ............... G02B 6/0008 |
| | | 362/108 |
| 2016/0146450 A1* | 5/2016 | Benhamou .......... F21V 23/0485 |
| | | 362/555 |
| 2016/0148479 A1 | 5/2016 | Harris |
| 2020/0383397 A1* | 12/2020 | Bean .................... H05B 1/0272 |

\* cited by examiner

SAFETY-MONITORING GARMENT SYSTEM

The current application claims a priority to the U.S. provisional patent application Ser. No. 63/000,377 filed on Mar. 26, 2020.

FIELD OF THE INVENTION

The present invention generally relates to safety gear. More specifically, the present invention is a safety-monitoring garment system.

BACKGROUND OF THE INVENTION

High visibility clothing comprise different garments fitted with means of providing illumination to the wearer. It is common for people to wear high visibility garments in situations where it is imperative for the wearer to be clearly spotted, such as constructions workers or public safety workers. In general, high visibility clothing comprise a mechanism which enables external light to reflect from the high visibility clothing. While the traditional reflective mechanism has been effective for most cases, the reflective mechanism is reliant on external sources of light. In dark conditions or during the nighttime, high visibility clothing is reliant on artificial sources of light, such as street lights or car lights, in order to make the wearer visible. If there is no artificial light, high visibility clothing can fail to make the wearer visible as even natural moonlight is not often enough. Some wearable accessories have been provided which provide artificial lighting to the wearer surroundings. However, these wearable accessories are often uncomfortable to be worn alongside a high visibility clothing, specially for working people in dangerous environments.

An objective of the present invention is to provide systems and methods for digitalization of high visibility clothing. The present invention provides means of illumination for high visibility clothing which do not rely on external sources of light. The present invention further provides means of tracking the users' performance, health conditions, and location support for employers or similar administrative users. The present invention meets current ANSI safety standards and provides integrated safety features with a separate layer of security for both administrative and non-administrative users. In addition, the present invention can provide customized designs for various applications, such as different occupations. For example, the present invention can be color coded for different occupations such as blue for law enforcement, red for medical rescue, or orange for highway maintenance. Furthermore, the present invention can provide additional environmental features such as user temperature exposure, noise/decibel exposure level, or similar environment exposure monitoring features that could affect the health of the user overtime.

DETAIL DESCRIPTIONS OF THE INVENTION

Figure 1:
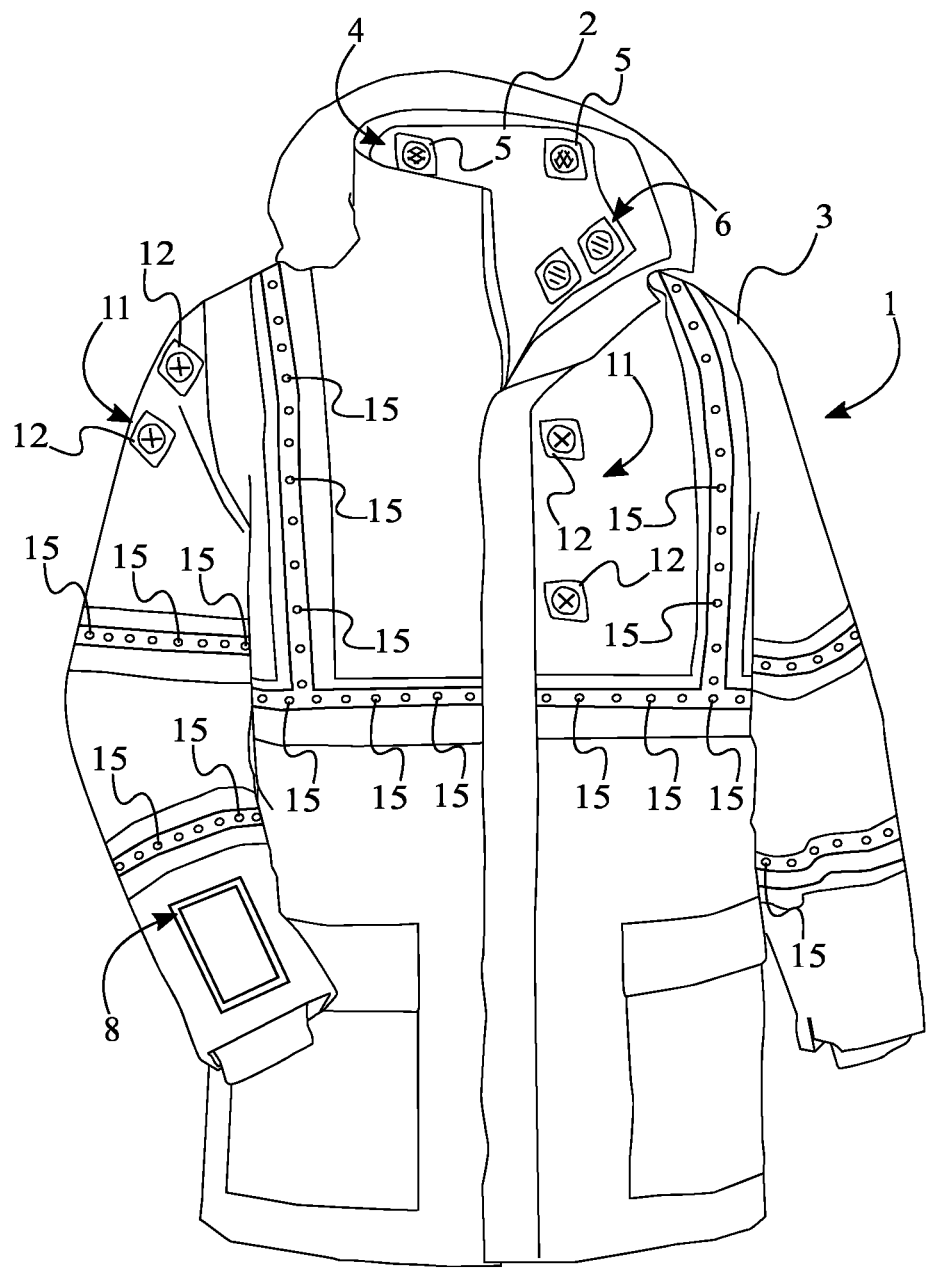
FIG. 1 is a front side view of the present invention.

All illustrations of the drawings are for the purpose of describing selected versions of the present invention and are not intended to limit the scope of the present invention.

The present invention is a safety-monitoring garment system that monitors and analyzes the health condition and safety of a user. The present invention provides constant and accurate readings in order to determine if the user is in any danger or needs immediate attention. The present invention may comprise a garment 1, at least one health-monitoring sensor 4, at least one performance-tracking sensor 6, a microcontroller 7, a user controller 8, and a portable power source 9, seen in FIG. 1, FIG. 2, and FIG. 3. The garment 1 surrounds the body of a user, preferably the upper body of the user. Moreover, the garment 1 protects the body of a user as the user is preferably a worker or an employee working in a hazardous environment. The garment 1 comprises an inner surface 2 and an outer surface 3. The inner surface 2 presses against the body of the user, and the outer surface 3 protects the user from the surrounding environment. The garment 1 may further comprise a plurality of layers to better protect the user. The plurality of layers may be, but is not limited to, insulation layers, impact-resistant layers, and light-reflective layers. It is understood that multiple layers or types of layers may be integrated into the garment 1 for specific parts of the body. The at least one health-monitoring sensor 4 monitors the vitals of a user, and the at least one performance-tracking sensor 6 monitors the work performance of the user in addition to various performance stats. The microcontroller 7 manages the at least one health-monitoring sensor 4, the at least one performance-tracking sensor 6, and the user controller 8. Moreover, the microcontroller 7 preferably comprises a CPM software, a rechargeable battery, a temperature sensor, a gyroscope, RGB LED indicators, and a wireless transmitter. Furthermore, the microcontroller 7 has induction charging capabilities, BLE tracking, flashing alerts, shatterproof materials, and water-resistant layers. The user controller 8 allows the user to manage and review the data of the at least one health-monitoring sensor 4 and the at least one performance-tracking sensor 6. The portable power source 9 provides the necessary power for the at least one health-monitoring sensor 4, the at least one performance-tracking sensor 6, the microcontroller 7, and the user controller 8.

The overall configuration of the aforementioned components allows the health and performance of a user to be accurately and constantly monitored. In order to retrieve accurate data while a user is wearing the garment 1, the at least one health-monitoring sensor 4 and the at least one performance-tracking sensor 6 is integrated into the inner surface 2, seen in FIG. 1. The microcontroller 7 is integrated into the garment 1 in order to protect the microcontroller 7 and provide direct connection to the at least one health-monitoring sensor 4, the at least one performance-tracking sensor 6, the user controller 8, and the portable power source 9. The user easily accesses and views the user controller 8 as the user controller 8 is integrated into the outer surface 3. In order to collect and process data, the at least one health-monitoring sensor 4, the at least one performance-tracking sensor 6, and the user controller 8 are electronically connected with the microcontroller 7. In order to function, the at least one health-monitoring sensor 4, the at least one performance-tracking sensor 6, the user controller 8, and the microcontroller 7 are electrically connected with the portable power source 9.

Figure 2:
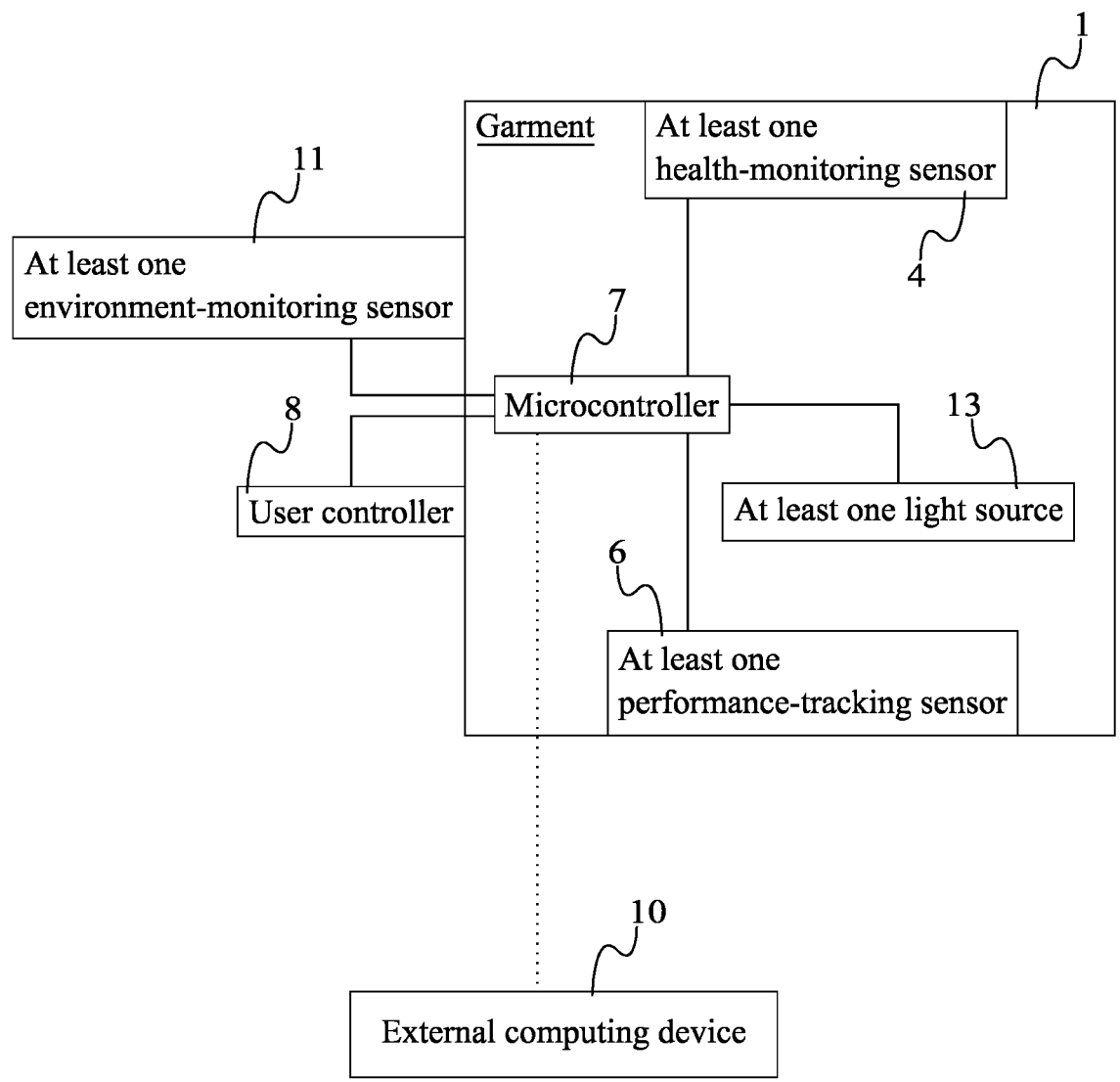
FIG. 2 is a schematic view of the electronic connections of the present invention.

In order for a supervisor to effectively monitor and oversee the safety of each employee simultaneously, the present invention may further comprise an external computing device 10, seen in FIG. 2. The external computing device 10 may be, but is not limited to, a smart device, a laptop, and a computer. The external computing device 10 is typically accessible by a supervisor or emergency responder with the necessary credentials. As the external computing device 10 is operated by an individual not wearing the garment 1 and is remotely positioned from the user with the garment 1, the external computing device 10 is positioned offset from the garment 1. The microcontroller 7 is communicably coupled with the external computing device 10, thereby wirelessly transmitting the data from the microcontroller 7 to the external computing device 10. In further embodiments of the present invention, a supplementary computing device may be utilized to manage the microcontroller 7 by the user wearing the garment 1. For example, a smart watch may be worn by the user, and the smart watch preferably provides additional functional capabilities and analysis.

In the preferred embodiment of the present invention, the at least one health-monitoring sensor 4 is a plurality of vital sensors 5, seen in FIG. 1. The plurality of vital sensors 5 allows the present invention to directly come into contact with specific body parts or areas of the body for an accurate reading, the plurality of vital sensors 5 is distributed about the garment 1. The plurality of vital sensors 5 includes a temperature sensor, a blood pressure sensor, a heart rate monitor, and a bloodwork sensor, thereby providing a comprehensive analysis of the current state of the health of the user.

Figure 3:
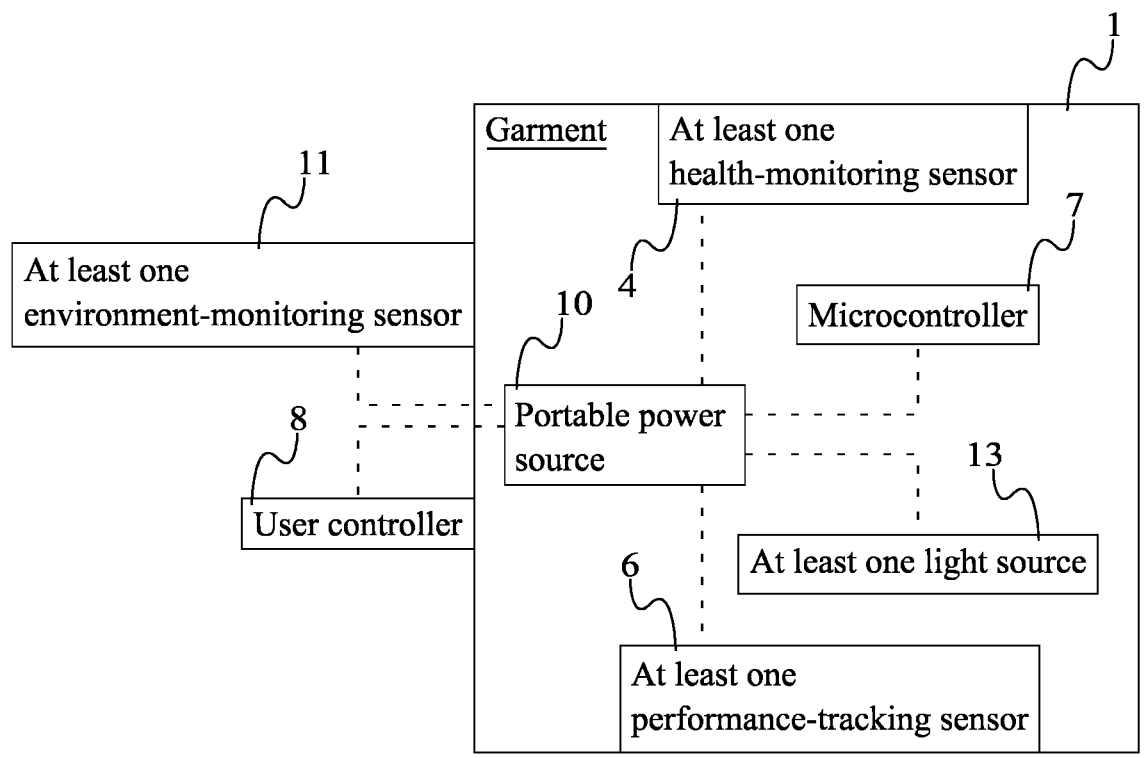
FIG. 3 is a schematic view of the electrical connections of the present invention.

The overall safety of a user is further enhanced as the present invention may further comprise at least one environment-monitoring sensor 11, seen in FIG. 1, FIG. 2, and FIG. 3. The at least one environment-monitoring sensor 11 detects any dangerous and hazardous conditions that allows a supervisor or emergency responder to assess and possibly change course of action. As the at least one environment-monitoring sensor 11 monitors the surrounding environment, the at least one environment-monitoring sensor 11 must be exposed to the surrounding environment. The at least one environment-monitoring sensor 11 is therefore integrated into the outer surface 3. The data is retrieved, stored, and analyzed as the at least one environment-monitoring sensor 11 is electronically connected to the microcontroller 7. The at least one environment-monitoring sensor 11 is able to function as the at least one environment-monitoring sensor 11 is electrically connected to the portable power source 9, thereby receiving the necessary power.

Similarly, in order to provide a comprehensive analysis of the surrounding environment, the at least one environment-monitoring sensor 11 is preferably a plurality of environment-monitoring sensors 12, seen in FIG. 1. The plurality of environment-monitoring sensors 12 is distributed about the garment 1 in order to accommodate each type of the plurality of environment-monitoring sensors 12. The plurality of environment-monitoring sensors 12 includes a temperature sensor, a decibel meter, an inertial measurement unit, and a proximity sensor.

Figure 4:
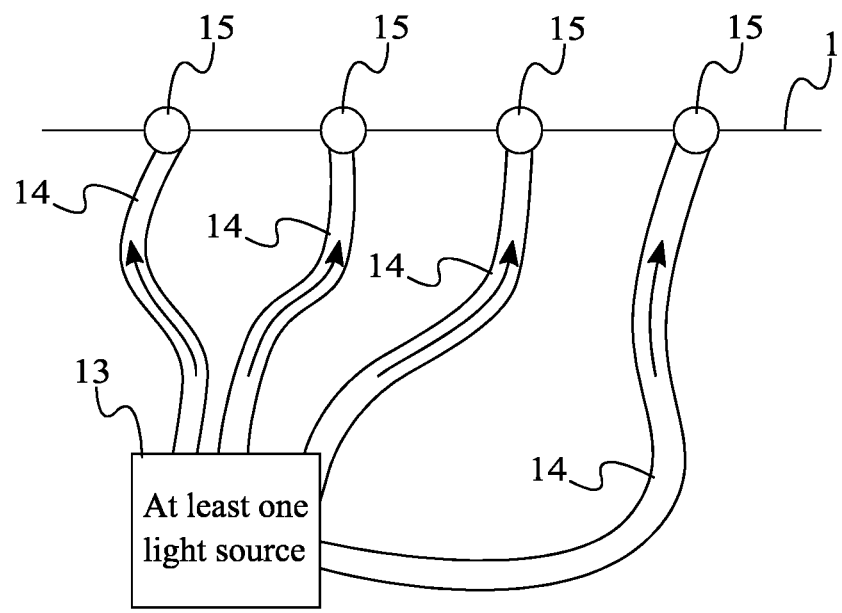
FIG. 4 is a schematic view of optical connections of the present invention.

Individuals within the surrounding environment are constantly made aware of the position of a user with the garment 1 as alternate embodiments of the present invention further comprise at least one light source 13, a plurality of optical cables 14, and a plurality of light outputs 15, seen in FIG. 4. The at least one light source 13 supplies the plurality of light outputs 15 with light. The plurality of optical cables 14 delivers the light from the at least one light source 13 to the plurality of light outputs 15. The plurality of light outputs 15 enhances the safety of a user by visually alerting nearby and passing individuals of the user regardless of the conditions of the surrounding environment. The plurality of light outputs 15 illuminates the garment 1 in dark environments, rainy environment, foggy environments, and so on. In order to house and protect the at least one light source 13, the at least one light source 13 is integrated into the garment 1. Individuals around the user with the garment 1 are visually alerted as the plurality of light outputs 15 is integrated into the outer surface 3 and is distributed about the garment 1. In order for the plurality of optical cables 14 to illuminate, the at least one light source 13 is in optical communication with each of the plurality of light outputs 15 by a corresponding cable from the plurality of optical cables 14. The at least one light source 13 is managed by the user with the user controller 8 as the at least one light source 13 is electronically connected with the microcontroller 7. The at least one light source 13 is sufficiently supplied with power as the at least one light source 13 is electrically connected with the portable power source 9.

Although the invention has been explained in relation to its preferred embodiment, it is to be understood that many other possible modifications and variations can be made without departing from the spirit and scope of the invention as hereinafter claimed.

What is claimed is:

1. A safety-monitoring garment system comprises:
   a garment;
   at least one health-monitoring sensor;
   at least one performance-tracking sensor;
   a microcontroller;
   a user controller;
   a portable power source;
   at least one environment-monitoring sensor;
   the garment comprises an inner surface and an outer surface;
   the at least one health-monitoring sensor and the at least one performance-tracking sensor being integrated into the inner surface, adjacent to a neck-receiving opening of the garment;
   the microcontroller being integrated into the garment;
   the user controller being integrated into the outer surface;
   the at least one health-monitoring sensor, the at least one performance-tracking sensor, and the user controller being electronically connected with the microcontroller;
   the at least one health-monitoring sensor, the at least one performance-tracking sensor, the user controller, and the microcontroller being electrically connected with the portable power source;
   the at least one health-monitoring sensor being a plurality of vital sensors;
   the plurality of vital sensors being distributed about the garment;
   the plurality of vital sensors comprises a temperature sensor, a blood pressure sensor, a heart rate monitor, and a bloodwork sensor;
   the at least one environment-monitoring sensor being integrated into the outer surface;
   the at least one environment-monitoring sensor being electronically connected to the microcontroller;
   the at least one environment-monitoring sensor being electrically connected to the portable power source;
   the at least one environment-monitoring sensor being a plurality of environment-monitoring sensors;
   the plurality of environment-monitoring sensors being distributed about the garment; and,
   the plurality of environment-monitoring sensors includes a temperature sensor, a decibel meter, an inertial measurement unit, and a proximity sensor.

2. The safety-monitoring garment system as claimed in claim 1 comprises:

an external computing device;
the external computing device being positioned offset from the garment; and,
the microcontroller being communicably coupled with the external computing device.

3. The safety-monitoring garment system as claimed in claim 1, wherein the garment comprises a plurality of layers.

4. The safety-monitoring garment system as claimed in claim 3, wherein the plurality of layers comprises at least one insulation layer, at least one impact-resistant layer, and at least one light-reflective layer.

5. The safety-monitoring garment system as claimed in claim 1 comprises:
a portable computing device;
the portable computing device being positioned adjacent to the garment; and,
the microcontroller being communicably coupled with the portable computing device.

6. The safety-monitoring garment system as claimed in claim 1, wherein the microcontroller comprises at least one rechargeable battery, at least one temperature sensor, at least one gyroscope, at least one red-green-blue (RGB) light-emitting-diode (LED) indicators, and at least one wireless transmitter.

7. The safety-monitoring garment system as claimed in claim 1 comprises:
at least one light source;
a plurality of optical cables;
a plurality of light outputs;
the at least one light source being integrated into the garment;
the plurality of light outputs being integrated into the outer surface;
the plurality of light outputs being distributed about the garment;
the at least one light source being in optical communication with each of the plurality of light outputs by a corresponding cable from the plurality of optical cables;
the at least one light source being electronically connected with the microcontroller; and,
the at least one light source being electrically connected with the portable power source.

8. A safety-monitoring garment system comprises:
a garment;
at least one health-monitoring sensor;
at least one performance-tracking sensor;
a microcontroller;
a user controller;
a portable power source;
at least one environment-monitoring sensor;
at least one light source;
a plurality of optical cables;
a plurality of light outputs;
the garment comprises an inner surface and an outer surface;
the at least one health-monitoring sensor and the at least one performance-tracking sensor being integrated into the inner surface, adjacent to a neck-receiving opening of the garment;
the microcontroller being integrated into the garment;
the user controller being integrated into the outer surface;
the at least one health-monitoring sensor, the at least one performance-tracking sensor, and the user controller being electronically connected with the microcontroller;
the at least one health-monitoring sensor, the at least one performance-tracking sensor, the user controller, and the microcontroller being electrically connected with the portable power source;
the at least one health-monitoring sensor being a plurality of vital sensors;
the plurality of vital sensors being distributed about the garment the plurality of vital sensors comprises a temperature sensor, a blood pressure sensor, a heart rate monitor, and a bloodwork sensor;
the at least one environment-monitoring sensor being integrated into the outer surface;
the at least one environment-monitoring sensor being electronically connected to the microcontroller;
the at least one environment-monitoring sensor being electrically connected to the portable power source;
the at least one environment-monitoring sensor being a plurality of environment-monitoring sensors;
the plurality of environment-monitoring sensors being distributed about the garment;
the plurality of environment-monitoring sensors includes a temperature sensor, a decibel meter, an inertial measurement unit, and a proximity sensor;
the at least one light source being integrated into the garment;
the plurality of light outputs being integrated into the outer surface;
the plurality of light outputs being distributed about the garment;
the at least one light source being in optical communication with each of the plurality of light outputs by a corresponding cable from the plurality of optical cables;
the at least one light source being electronically connected with the microcontroller; and,
the at least one light source being electrically connected with the portable power source.

9. The safety-monitoring garment system as claimed in claim 8 comprises:
an external computing device;
the external computing device being positioned offset from the garment; and,
the microcontroller being communicably coupled with the external computing device.

10. The safety-monitoring garment system as claimed in claim 8, wherein the garment comprises a plurality of layers.

11. The safety-monitoring garment system as claimed in claim 10, wherein the plurality of layers comprises at least one insulation layer, at least one impact-resistant layer, and at least one light-reflective layer.

12. The safety-monitoring garment system as claimed in claim 8 comprises:
a portable computing device;
the portable computing device being positioned adjacent to the garment; and,
the microcontroller being communicably coupled with the portable computing device.

13. The safety-monitoring garment system as claimed in claim 8, wherein the microcontroller comprises at least one rechargeable battery, at least one temperature sensor, at least one gyroscope, at least one RGB LED indicators, and at least one wireless transmitter.

* * * * *